(12) United States Patent
Lui et al.

(10) Patent No.: US 8,835,645 B2
(45) Date of Patent: Sep. 16, 2014

(54) PROCESS FOR PREPARING CYANIMINO-1,3-THIAZOLIDINES

(75) Inventors: Norbert Lui, Odenthal (DE); Klaus Jelich, Wuppertal (DE); Martin Littmann, Leverkusen (DE); Klaus Lorenz, Weiterstadt (DE); Brice Lecorre, Düsseldorf (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/677,462

(22) PCT Filed: Sep. 2, 2008

(86) PCT No.: PCT/EP2008/007141
§ 371 (c)(1),
(2), (4) Date: Mar. 10, 2010

(87) PCT Pub. No.: WO2009/033583
PCT Pub. Date: Mar. 19, 2009

(65) Prior Publication Data
US 2010/0190995 A1    Jul. 29, 2010

(30) Foreign Application Priority Data

Sep. 14, 2007   (EP) ..................... 07116434

(51) Int. Cl.
*C07D 277/06*   (2006.01)
*C07D 277/18*   (2006.01)

(52) U.S. Cl.
CPC .................. *C07D 277/18* (2013.01)
USPC ...................................... 548/198

(58) Field of Classification Search
None
See application file for complete search history.

(56) References Cited

FOREIGN PATENT DOCUMENTS

| DE | 2 205 745 | 8/1973 |
| EP | 1 460 068 | 9/2004 |
| WO | WO03057681 A1 * | 7/2003 |

OTHER PUBLICATIONS

International Search Report and Written Opinion, PCT/EP2008/007141, Sep. 2, 2008, 14 pages.
Maienfisch et al., "Azido-Neonicotinoids as Candidate Photoaffinity Probes for Insect Nicotinic Actetylcholine Receptors," *Chima* 57(11):710-714 (2003).
Neidlein et al., Reaktionsverhalten von N-Cyanimido-dithiokohlenseauereester und 2,2-Bismethylmercapto-1-Cyanacrylnitril, *Archiv der Pharmazie* 305:731-737 (1972).
Zhang et al., "Insect Nicotinic Acetylcholine Receptor: Conserved Neonicotinoid Specificity of [³H]Imidacloprid Binding Site," *Journal of Neurochemistry* 75(3):1294-1303 (2000).

* cited by examiner

*Primary Examiner* — Nyeemah A Grazier
(74) *Attorney, Agent, or Firm* — Sterne, Kessler, Goldstein & Fox P.L.L.C.

(57) ABSTRACT

The present invention relates to a process for preparing cyanimino-1,3-thiazolidines, which are important building blocks for the preparation of crop protection active ingredients and pharmaceuticals, by the following scheme:

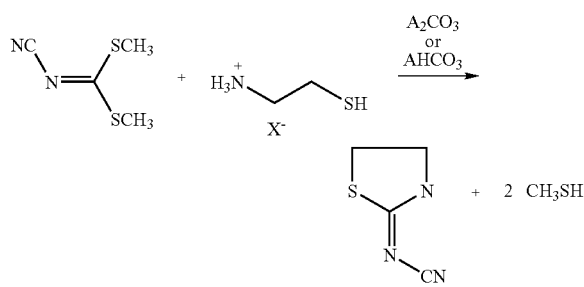

where A is an alkali metal and X represents an acid radical.

7 Claims, No Drawings

PROCESS FOR PREPARING CYANIMINO-1,3-THIAZOLIDINES

The present invention relates to a process for preparing cyanimino-1,3-thiazolidines, which are important building blocks for the preparation of crop protection active ingredients and pharmaceuticals.

It is known that cyanimino-1,3-thiazolidine is obtained when dimethyl N-cyanocarbonimidodithiocarbonate and cysteamine are heated in ethanol under reflux (cf. Archiv der Pharmazie 305, 731 (1972) and DE 2205745).

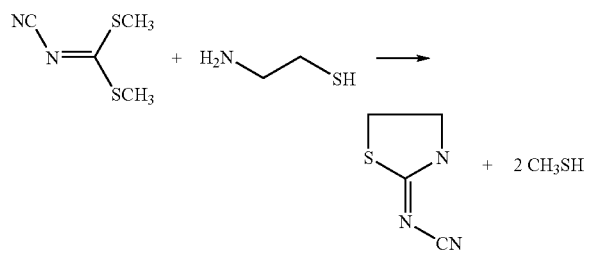

The yields described there are too low for an industrial preparation of the product. EP 1 460 068 A1 describes the reaction of dimethyl N-cyanocarbonimidodithiocarbonate and cysteamine in the presence of alkali metal hydroxides. A disadvantage of this process is the high basicity of the alkali metal hydroxides which, in the case of inexact dosage, leads to product losses and hence poorer yields.

A further process is described in Chimia (Chimia 2003, 57, No 11, 710-714). This describes the reaction with sodium hydrogencarbonate in ethanol at 40° C.

With regard to the disadvantages and problems outlined above, there is a need to provide a process which, proceeding from dimethyl N-cyanocarbonimidodithiocarbonate, makes cyanimino-1,3-thiazolidine obtainable with high yields and high selectivity.

There is also a need to provide a process in which the recovery of methyl mercaptan is enabled, since this substance is required as a raw material.

This object is achieved by the following process. Dimethyl N-cyanocarbonimidodithiocarbonate and 2-aminoethanethiol or a salt thereof (formula (I))

(I)

are reacted in the presence of water and alkali metal carbonates or alkali metal hydrogencarbonates to give cyanimino-1,3-thiazolidine of the formula (II).

(II)

In this compound, X represents an acid radical, for example halogen, acetate, sulphate or hydrogensulphate.

The reaction proceeds according to scheme 1

Scheme 1

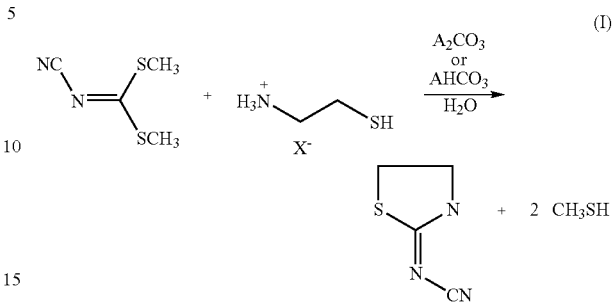

where A is an alkali metal.

It is surprising that, in the presence of alkali metal carbonates or hydrogencarbonates and water, the reaction proceeds at comparatively low temperatures between 5-15° C. The product is formed in a high yield. The continuous release of gaseous methyl mercaptan enables recovery in industrial scale production, for example by condensation.

Preference is given to performing the process according to the invention using compounds of the formula (I) in which X is an acid radical, for example halogen, acetate, sulphate or hydrogensulphate.

X is preferably chloride, sulphate or hydrogensulphate.

For the process according to the invention, alkali metal carbonates or alkali metal hydrogencarbonates are used. Preference is given to using sodium hydrogencarbonate, potassium hydrogencarbonate, sodium carbonate and potassium carbonate. Particular preference is given to sodium hydrogencarbonate and sodium carbonate.

The cysteamine salts of the formula (I) for use as starting materials in the process according to the invention are commercially available and are commonly known compounds in organic chemistry.

The process according to the invention proceeds in the presence of water. It is also possible to use aqueous solvent mixtures. As well as water, these may also contain other solvents. Examples include: halohydrocarbons, especially chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols such as methanol, ethanol, isopropanol, butanol; ethers such as ethyl propyl ether, methyl tert-butyl ether, methyl n-butyl ether, anisole, phenetol, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, dioxane, dichlorodiethyl ether, and polyethers of ethylene oxide and/or of propylene oxide; amines such as trimethyl-, triethyl-, tripropyl- and tributylamine, N-methylmorpholine, pyridine, alkylated pyridines and tetramethylenediamine; nitrohydrocarbons such as nitromethane, nitroethane, nitropropane, nitrobenzene, chloronitrobenzene, o-nitrotoluene; nitriles such as acetonitrile, methyl nitrile, propionitrile, butyronitrile, isobutyronitrile, benzonitrile, phenyl nitrile, m-chlorobenzonitrile, and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methyl ethyl, ethyl propyl, ethyl isobutyl and pentamethylene sulphone; aliphatic, cycloaliphatic or aromatic hydrocarbons such as pentane, hexane, heptane, octane, nonane; for example so-called white spirits with components having boiling points in the range, for example, of 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene; esters such as methyl, ethyl, butyl and isobutyl acetate, and dimethyl, dibutyl and ethylene carbonate; amides such as hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2 (1H)-pyrimidine, octylpyrrolidone, octylcaprolactam, 1,3-dimethyl-2-imidazolinedione, N-formylpiperidine, N,N'-1, 4-diformylpiperazine; ketones such as acetone, acetophenone, methyl ethyl ketone, methyl butyl ketone.

In addition, the process according to the invention can proceed in aqueous biphasic systems. In this case, a further solvent of zero or only very limited water miscibility is used.

Preferred solvents which can be used together with water are: methanol, ethanol, THF, butanol.

In a preferred embodiment, the solvent consists of water to an extent of at least 50%.

In a particularly preferred embodiment, the solvent consists of water to an extent of at least 95%.

In a very particularly preferred embodiment, the solvent used is only water.

The cysteamine hydrochloride or the cysteamine is dissolved in a solution of alkali metal carbonates or alkali metal hydrogencarbonates. This operation can proceed at room temperature. Subsequently, the solution is cooled to 5-15° C., preferably 10° C. The dimethyl N-cyanocarbonimidodithiocarbonate is metered in.

The molar ratio of cysteamine hydrochloride to dimethyl N-cyanocarbonimidodithiocarbonate is preferably in the range from 1:0.7 to 1:1.5. Particular preference is given to a range from 1:0.95 to 1:1.05.

After the metered addition has ended, the reaction mixture is stirred at temperatures of 10-15° C. for another 0.5-10 hours. Preference is given to 1-4 hours. However, longer reaction times are uncritical.

On completion of the reaction, the pH of the solution can be adjusted to 4 to 6 by means of an acid. This step is not essential for the performance of the process, but may lead to higher yields. The acid used may be an inorganic acid or an organic acid. For example, hydrochloric acid, phosphoric acid, sulphuric acid or nitric acid can be used.

The process according to the invention can be performed batchwise or continuously. In addition, the process can be performed under standard pressure, reduced pressure or elevated pressure.

The workup can be effected by filtration. This also removes the methyl mercaptan. A complicated distillation as described in the prior art is not necessary as a result.

The process according to the invention for preparing cyanimino-1,3-thiazolidine is described in the examples which follow, which further illustrate the above description. However, the examples should not be interpreted in a restrictive way.

PREPARATION EXAMPLES

Example 1

Into a solution of 26.5 g of sodium carbonate in 150 ml of water are metered, at room temperature, 28.8 g of cysteamine hydrochloride. The reaction mixture is cooled to 10° C. and 37.1 g of dimethyl N-cyanocarbonimidodithiocarbonate are metered in. After the end of the metered addition, the mixture is stirred at 10° C. for a further 2 hours and then heated to 20° C. At 20° C., 37 g of 20% hydrochloric acid are added dropwise. The mixture is then filtered and the solids are washed with 100 ml of water. After drying under reduced pressure, 30.3 g of cyanimino-1,3-thiazolidine are obtained (corresponds to a yield of 94.7%).

Example 2

Into a solution of 26.5 g of sodium carbonate in 150 ml of water are metered, at room temperature, 28.8 g of cysteamine hydrochloride. The reaction mixture is cooled to 10° C. and 37.1 g of dimethyl N-cyanocarbonimidodithiocarbonate are metered in. After the end of the metered addition, the mixture is stirred at 10° C. for a further 2 hours and then heated to 20° C. The mixture is subsequently filtered and the solids are washed with 2×100 ml of water. After drying under reduced pressure, 29.8 g of cyanimino-1,3-thiazolidine are obtained (corresponds to a yield of 93%).

Example 3

Into a solution of 23.8 g of sodium hydrogencarbonate in 200 ml of water are metered, at room temperature, 28.8 g of cysteamine hydrochloride. The reaction mixture is cooled to 10° C. and 37.1 g of dimethyl N-cyanocarbonimidodithiocarbonate are metered in. After the end of the metered addition, the mixture is stirred at 10° C. for a further 3 hours and then heated to 20° C. The mixture is then filtered and the solids are washed with 100 ml of water. After drying under reduced pressure, 29.4 g of cyanimino-1,3-thiazolidine are obtained (corresponds to a yield of 92%).

The invention claimed is:

1. A process for preparing cyanimino-1,3-thiazolidine comprising reacting dimethyl N-cyanocarbonimidodithiocarbonate and a salt of cysteamine in the presence of at least one alkali metal carbonate or alkali metal hydrogencarbonate in a solvent, wherein the solvent comprises at least 95% water, and wherein the reaction proceeds within a temperature range of 5-15° C.

2. A process according to claim 1, wherein the solvent used is only water.

3. A process according to claim 1, wherein the molar ratio of dimethyl N-cyanocarbonimidodithiocarbonate to salts of cysteamine is in the range from 1:0.7 to 1:1.5.

4. A process according to claim 1, wherein the alkali metal carbonate is selected from the group consisting of sodium carbonate and potassium carbonate, and the alkali metal hydrogencarbonate is selected from the group consisting of sodium hydrogencarbonate and potassium hydrogencarbonate.

5. A process according to claim 2, wherein the molar ratio of dimethyl N-cyanocarbonimidodithiocarbonate to salts of cysteamine is in the range from 1:0.7 to 1:1.5.

6. A process according to claim 2, wherein the alkali metal carbonate is selected from the group consisting of sodium carbonate and potassium carbonate, and the alkali metal hydrogencarbonate is selected from the group consisting of sodium hydrogencarbonate and potassium hydrogencarbonate.

7. A process according to claim 3, wherein the alkali metal carbonate is selected from the group consisting of sodium carbonate and potassium carbonate, and the alkali metal hydrogencarbonate is selected from the group consisting of sodium hydrogencarbonate and potassium hydrogencarbonate.

\* \* \* \* \*